(12) United States Patent
Cheetham et al.

(10) Patent No.: US 6,844,019 B1
(45) Date of Patent: Jan. 18, 2005

(54) FLAVOR/AROMA MATERIALS AND THEIR PREPARATION

(75) Inventors: Peter Samuel James Cheetham, Tunbridge Wells (GB); Michelle Lorraine Gradley, Canterbury (GB); John Thomas Sime, Ashford (GB)

(73) Assignee: Zylepsis Limited, Kent (GB)

( * ) Notice: Subject to any disclaimer, the term of this patent is extended or adjusted under 35 U.S.C. 154(b) by 0 days.

(21) Appl. No.: 09/914,224

(22) PCT Filed: Feb. 24, 2000

(86) PCT No.: PCT/GB00/00654

§ 371 (c)(1),
(2), (4) Date: Aug. 23, 2001

(87) PCT Pub. No.: WO00/50622

PCT Pub. Date: Aug. 31, 2000

(30) Foreign Application Priority Data

Feb. 24, 1999 (GB) .............................................. 9904251

(51) Int. Cl.⁷ .............................. A23L 1/23; C12N 1/20
(52) U.S. Cl. ..................... 426/534; 435/253.3; 435/156
(58) Field of Search ............................ 435/253.3, 156, 435/137; 426/534, 7, 538

(56) References Cited

U.S. PATENT DOCUMENTS 3,817,830 A * 6/1974 Hegeman et al. ........... 435/280
5,279,950 A * 1/1994 Labuda et al. .............. 435/147

FOREIGN PATENT DOCUMENTS

| EP | 0 857 789 | 8/1998 |
|----|-----------|--------|
| EP | 0 885 968 | 12/1998 |
| GB | 2 301 103 | 11/1996 |
| WO | WO 94/02621 | 2/1994 |
| WO | WO 94/13614 | 6/1994 |
| WO | WO 96/08576 | 3/1996 |
| WO | 96/39859 | * 12/1996 |
| WO | 97/35999 | * 10/1997 |

OTHER PUBLICATIONS

Faulds et al. "Release of ferulic acid from wheat bran by a ferulic acid esterase (FAE–II) from *Aspergillus niger*"; Appl. Microb. Biotech. 43(6): 1082–1087, Jun. 1995.*

Faulds, C.B. et al. "Release of Ferulic Acid from Wheat Bran by a Ferulic Acid Esterase (FAE–III) from *Aspergillus niger*"; Applied Microbiology and Biotechnology, 43(6) 1082–1087 (1995).

* cited by examiner

*Primary Examiner*—Keith Hendricks
(74) *Attorney, Agent, or Firm*—Dann Dorfman Herrell and Skillman, P.C.

(57) ABSTRACT

Flavor components, particularly for a vanilla composition, are produced by essentially natural methods employing biotransformation of plant-derived materials. Ferulic acid, a component of many plant cell walls, may be converted into vanillin, directly or indirectly. A plurality of such compounds may undergo bioconversions to produce components of a flavor composition.

21 Claims, No Drawings

FLAVOR/AROMA MATERIALS AND THEIR PREPARATION

This application is a 35 U.S.C. §371 application which claims priority to PCT/GB00/00654 filed Feb. 24, 2000 which in turn claims priority to GB application number 9904251.7 filed Feb. 24, 1999, the disclosure of each of these applications being incorporated herein by reference.

BACKGROUND

The present invention relates to flavour/aroma materials and the preparation of such materials and key intermediates. It is particularly (though not exclusively) concerned with vanilla flavour materials and related materials.

Supplies of natural vanilla bean extracts suffer from shortages of supply and variability in quality. Despite a wide range of natural flavour chemicals having become commercially available over the last 10–15 years, no entirely satisfactory natural vanillin flavour chemical product or vanilla flavour has yet been developed. The main difficulties in developing a cost-effective vanillin product are firstly the unavailability of the preferred raw material, ferulic acid; and secondly the difficulty in finding microbial strains that can accumulate vanillin due to its ease of further metabolism, for instance to vanillic acid, and its inhibitory effect on the metabolism of cells. The main difficulty in developing a natural vanilla flavour is the large number of different chemicals that together contribute to the superior flavour and aroma of vanilla bean extracts. In addition for the minor usage of vanilla in fragrances a colourless solid product is required rather than the coloured ethanol-water vanilla bean extracts.

Our earlier application WO-A-96/39859 discloses the production of some phenolic materials by the enzymatic hydrolysis of plant materials. Thus ferulic acid (1a) was produced by enzyme treatment of wheat germ or wheat bran. Caffeic acid (1b) was produced by enzyme treatment of sunflower meal. Ferulic acid and esters thereof are valuable as precursor compounds and also as ingredients of foods and cosmetics, e.g. serving as antioxidants.

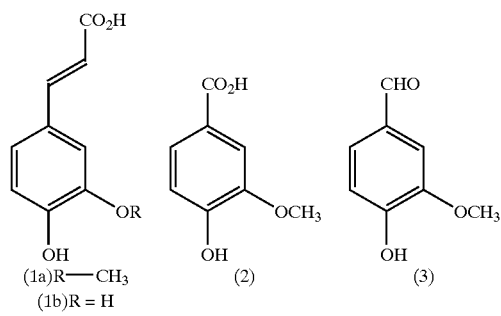

Various workers have reported the microbial conversion of ferulic acid (1a) into vanillin (3) either directly (e.g. DE-A-19532317) or via vanillic acid (2) (FR-A-2724394).

OUTLINE OF THE INVENTION

The invention provides, inter alia, a method of converting a first composition comprising one or more species of formula (A) into a second composition comprising one or more species of formula (B):

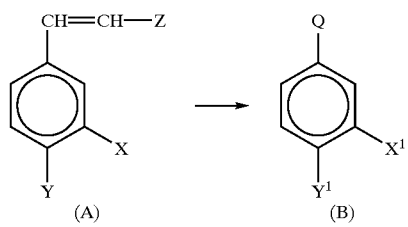

where X, Y, X' and Y' are independently selected from H, OH and OMe; Z is $CO_2H$, $CO_2$carb (where carb represents a carbohydrate residue), CHO or $CH_2OH$, and Q is CHO, $CO_2H$ or $CH_2OH$, said method comprising treating said first composition with one or more microorganisms under conditions such that (A) is converted into (B); said microorganism(s) being selected, from (a) *Pseudomonas putida*; (b) Rhodotorula species and other yeasts capable of converted ferulic acid into vanillic acid; (c) microorganisms possessing both ferulic acid esterase activity and intra-sidechain cleavage activity such that they are capable of converting ferulic acid glycosides into vanillin and/or vanillic acid; and (d) *Micromucor isabellinus* or *Aspergillus fumigatus* strains capable of converting vanillic acid into vanillin.

The process may include a preliminary step of obtaining said first composition comprising ferulic acid from a plant material by a process comprising:
(a) treating the plant material to produce a solution containing a ferulic acid ester; and
(b) treating said solution with an enzyme composition having ferulic acid esterase activity under conditions such that ferulic acid esters are converted into ferulic acid. N.B the esters generally involve carbohydrate residues, particularly sugar residues, and are sometimes termed glycosides.

The invention further provides several microorganisms useful in methods of the invention. These include several deposited strains and mutants thereof (which may be produced by chemical or other conventional mutagenesis or by genetic engineering). As well as intact organisms, use may be made of extracts and isolated enzymes.

Aspects of the present invention include the following.
A) A process for use in preparing a flavour/aroma composition containing a plurality of flavour/aroma components, said process having the step(s) of
(i) treating a plant material or plurality of plant materials to produce a precursor compound and preferably a plurality of precursor compounds (separately or mixed) preferably comprising two or more 1-phenylalkene species, preferably of formula (4):

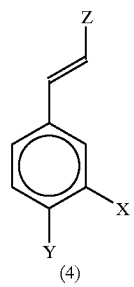

where X and Y are independently selected from H, OH and OMe and Z is $CO_2H$, $CO_2$carb (where carb represents a carbohydrate residue) CHO or $CH_2OH$, most preferably comprising the compound (4) wherein X=OMe, Y=OH and Z=$CO_2H$ (ferulic acid) and preferably also the compounds wherein X=H, Y=OH and Z=$CO_2H$ (coumaric acid) and X=OH, Y=OH and Z=$CO_2H$ (caffeic acid); and preferably ii) subjecting said precursor compound or compounds (with or without separation from the plant material residues) to one or more biotransformations to produce a flavour/aroma composition. For precursor compounds having a benzene ring bearing a substituent —CH:CH—$CO_2H$ (e.g. compounds of structure (4)), biotransformations may generate compounds in which this substituent has been converted into —$CO_2H$ and/or —$CH_2OH$ and/or —CHO.

The term "plant material" as used herein includes material such as the meal or pulp produced by mechanical processing of plants, and the residues left after extraction of seed oils etc.

Particularly preferred plant materials for step (i) include maize, wheat, rice, sugar beet and parts thereof, particularly waste materials from their normal uses e.g. rice bran and cereal fibres. For example maize fibre and wheat fibre may be derived from dry or wet milling. Sugar beet fibre may be derived from pulp. A mixture of plant materials may be employed to give a desired mixture of precursors.

Step (i) may involve:
(a) treatment of plant material (damp or dried) with acid (preferably citric acid, e.g. provided by addition of lemon or lime juice) to release glycosides of at least ferulic acid, generally with heating e.g. to 50–250°; and
(b) treatment of the glycoside-containing mixture with base (e.g. an alkali metal bicarbonate) or one or more enzymes with ferulic acid esterase ("FAE") activity to release ferulic acid. Suitable enzymes include Hemicellulase (from Amano, derived from *Aspergillus* spp.) and/or Celluzyme (Novo Nordisk) and/or enzymes from *Humicola insolens*, available as Pentopan, Biofeed Plus or Biofeed Beta (Novo Nordisk). These enzymes have some xylanase activity, in addition to their FAE activity. If required, additional sources of xylanase can be added to supplement the xylanase activity already present. (Note: the so-called glycosides of ferulic acid etc. are in fact esters of carbohydrate residues rather than conventional glycoside ethers).

In step (a), citric acid is suitable because it is reasonably strong, heat stable, cheap, active on a range of ferulic acid containing materials, non-volatile, and not inclined to cause side reactions. It is adequately soluble in the cereal "mashes". It can easily be recovered as an insoluble salt (e.g. calcium), for reuse. It is a "natural" material, which is approved for food use. Alternatives include other organic polycarboxylic acids, particularly hydroxyacids, such as isocitric, tartaric, malic, fumaric and succinic acids.

Solutions containing suitable acids may be used, e.g. a grape-derived solution containing tartaric acid; or a fermentation medium containing citric or malic acid.

A microorganism may provide the activities required to carry out step (i) (b) and step (ii) (biotransformation of ferulic acid and/or other precursor compounds). For example we have developed strains of *Aspergillus niger, A. flavus,* and *Penicillium chrysogenum* having both the necessary FAE and alkene cleavage activities for acting on the product of the step (a) to convert ferulic acid glycoside into vanillic acid.

Step (i) can also be effected by treatment of plant material (e.g. maize fibre) with aqueous alkali such as a hydroxide, carbonate or bicarbonate of an alkali metal or alkaline earth metal. Sodium bicarbonate is preferred.

A product mixture containing vanillic acid and other materials (e.g. p-hydroxybenzoic acid from coumaric acid) may undergo one or more further biotransformations without isolation of individual components, e.g. converting vanillic acid into vanillin and effecting corresponding transformations of other components.

B) Preparation of vanillin comprising the biotransformation of vanillic acid (2) into vanillyl alcohol (5), and the biotransformation of vanillyl alcohol (5) into vanillin (3). Generally the two steps will employ different microorganisms. N.B compounds such as vanillyl alcohol may be valuable flavour chemicals in their own right.

The steps may be novel in their own right. The reduction of vanillic acid to vanillyl alcohol may be effected by *Zygorhynchus moelleri*.

C) Preparation of vanillin comprising the biotransformation of vanillic acid (2) directly into vanillin (3) by means of strains of microorganisms such as *Aspergillus fumigatus* or *Micromucor isabellinus*.

D) Preparation of vanillin comprising the biotransformation of ferulic acid into vanillin, e.g. by a strain of *Pseudomonas putida*.

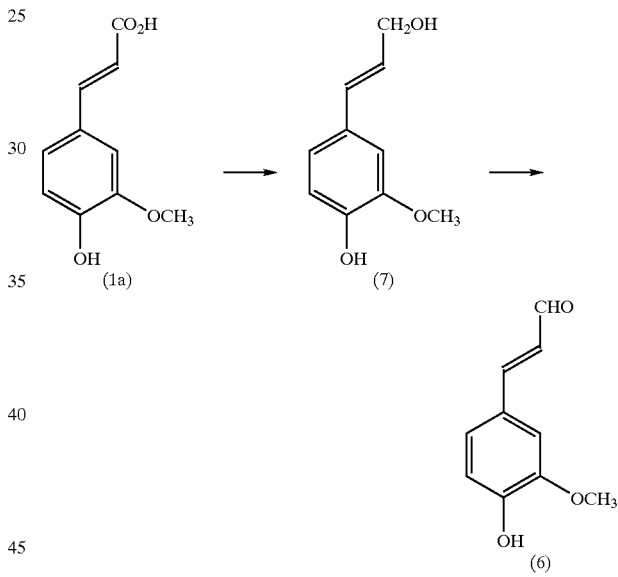

E) Preparation and isolation of substances, particularly substances prone to further reaction (e.g. aldehydes) or prone to inhibiting microorganisms (e.g. vanillin) by effecting a biotransformation using a microorganism in an aqueous phase which is brought into contact with a second phase into which products pass. This "in situ product removal" ("ISPR") may employ a vegetable oil as the second phase. Products may subsequently be recovered from the second phase, e.g. by crystallisation or solvent extraction. This process of ISPR can be employed in step (ii) of process A (above), or in processes B, C and D.

F) A vanilla flavour/aroma composition which is the product of a process according to (A) above or is a blend of one or more such products and/or one or more substances prepared by a process according to (B), (D), or (E), above and/or one or more vanilla flavour chemicals from other sources and/or a vanilla bean extract.

G) Use of *Pseudomonas putida* for converting ferulic acid into vanillic acid. The raw material is preferably the mixture obtained by treating plant material such as cereal fibre with citrate and FAE enzyme (as described in section A above), without isolation of the ferulic acid.

H) Various transformations as described above may be applied to other substrates. This may lead to further useful flavour/odour components. For example benzoic acid, 4-hydroxybenzoic acid and 3,4-dihydroxybenzoic acids can be converted into the corresponding aldehydes and/or benzyl alcohols.

I) A method of isolating strains of microorganisms for use in processes of the invention. Material (e.g. soil samples) containing a multiplicity of strains is used to produce a multiplicity of colonies, e.g. on agar, and individual colonies are tested for useful activity by means of a reagent suitable for detecting aldehydes. For example, 2,4-dinitrophenylhydrazine produces orange/red zones around aldehyde-producing colonies and a dark yellow zone around an alcohol producing colony.

J) Strains isolated by method I) and mutants thereof (obtained naturally, by conventional mutagenesis or by genetic engineering). This includes heterologous organisms which have been transformed so that they have derived activities of the "parent" organism from which the transforming nucleic acid was directly or indirectly derived.

Some particularly preferred strains have been deposited under the Budapest Treaty. Brief details follow. a) Strains deposited with NCIMB (NCIMB Ltd, 23 St Machar Drive, Aberdeen, A24 3RY, GB)
1. *Brevundimonas vesicularis* (Zyl 295)-NCIMB 40987- Gram negative bacterium (deposited Nov. 18, 1998)
2. *Pseudomonas putida* (Zyl 503)-NCIMB 40988-Gram negative bacterium (Nov. 18, 1998)
   b) Strains deposited with IMI (CABI Bioscience UK Centre Egham, Genetic Resource Collection, Bakeham Lane, Egham, Surrey TW20 9TY, GB)
1. *Rhodotorula glutinis* (Zyl 717)-IMI 379896-Yeast, producing a red/orange pigment (Nov. 20, 1998)
2. *Aspergillus flavus* (Zyl 714)-IMI 379895-Filamentous fungus producing light green spores (Nov. 20, 1998)
3. *Aspergillus fumigatus* (Zyl 747)-IMI 379902-Filamentous fungus producing blue/grey spores (Nov. 20, 1998)
4. *Trichoderma koningii* (Zyl 751)-IMI 379903-Filamentous fungus producing green spores (Nov. 20, 1998)
5. *Aspergillus niger* (Zyl 759)-IMI 379904-Filamentous fungus producing brown/black spores (Nov. 20, 1998)
6. *Micromucor isabellinus* (Zyl 849)-IMI 379893- Filamentous fungus producing pale brown spores (Nov. 20, 1998)
7. *Zygorhynchus moelleri* (Zyl 851)-IMI 379899- Filamentous fungus, with aerial hyphae producing black spores (Nov. 20, 1998)
8. *Penicillium chrysogenum* (Zyl 860)-IMI 379900- Filamentous fungus producing blue spores (Nov. 20, 1998)
9. *Pseudomonas putida* (Zyl 581)-IMI 382568, Gram negative bacterium; deposited Jan. 1, 2000

The use of those strains is illustrated in the following examples. Of course other strains of the same species may be used to carry out the same transformations.

The invention will now be explained in more detail, with reference to some specific examples.

General Experimental Conditions

In the following examples, where organisms are grown in culture broth, the growth medium can contain specified amounts of either, or both, of a vitamins supplement and a trace elements supplement.

These were prepared as follows.

Vitamins supplement: biotin (2 $mgL^{-1}$), folic acid (2 $mgL^{-1}$), pyridoxine (10 $mgL^{-1}$), riboflavin (5 $mgL^{-1}$) thiamine (5 $mgL^{-1}$), nicotinic acid (5 $mgL^{-1}$), pantothenic acid (5 $mgL^{-1}$), vitamin B12 (0.1 $mgL^{-1}$), 4-aminobenzoic acid (5 $mgL^{-1}$), and thioacetic acid (5 $mgL^{-1}$).

Trace elements supplement: concentrated hydrochloric acid (51.3 $mLL^{-1}$), MgO (10.75 $gL^{-1}$), $CaCO_3$ (2.0 $gL^{-1}$), $FeSO_4.7H_2O$ (4.5 $gL^{-1}$), $ZnSO_4.7H_2O$ (1.44 $gL^{-1}$), $MnSO_4.4H_2O$ (1.12 $gL^{-1}$), $CuSO_45H_2O$ (0.25 $gL^{-1}$), $CoSO_4.7H_2O$ (0.28 $gL^{-1}$), and $H_3BO_3$ (0.06 $gL^{-1}$).

Analysis of coniferyl alcohol, coniferaldehyde, caffeic acid, coumaric acid, ferulic acid, vanillic acid, vanillyl alcohol and vanillin was carried out using high performance liquid chromatography (hplc) using the following conditions:

| | |
|---|---|
| Column | Spherisorb $C_{18}$ |
| Mobile phase | 80:20 deionised water:acetonitrile containing 1% acetic acid |
| Flow rate | 1.75 mL $min^{-1}$ |
| Detection | Ultraviolet at 290 nm |

Analysis of 4-hydroxybenzoic acid and 4-hydroxybenzaldehyde was carried out using high performance liquid chromatography (hplc) using the following conditions:

| | |
|---|---|
| Column | Spherisorb $C_{-18}$ |
| Mobile phase | 80:20 deionised water:acetonitrile containing 1% acetic acid |
| Flow rate | 2 mL $min^{-1}$ |
| Detection | Ultraviolet at 275 nm |

Alternatively, analysis of 4-hydroxybenzoic acid and 4-hydroxybenzaldehyde was carried out using thin layer chromatography (tlc) using the following conditions: silica plates eluting with petroleum either (40–60): ethyl acetate (50:50) and visualisation with UV or dinitrophenylhydrazine solution (0.4% in 2M HCl).

A) Use of Plant Materials

Maize fibre is an example of a cheap raw material which can provide raw materials for use in the preparation of flavour/aroma materials. Treatment with alkali leads to the liberation of ferulic acid, and lesser amounts of other materials, notably coumaric acid. The mixture can be subjected to biotransformation, e.g. to produce a mixture of vanillic acid and 4-hydroxybenzoic acid, which could be subjected to further biotransformations, e.g. converting the carboxylic acid groups to —CHO and/or —$CH_2OH$.

EXAMPLE 1A

Ferulic and Coumaric Acids From Maize (a) Use of sodium hydroxide: to 500 g of ground maize fibre as added 1 liter of 1M sodium hydroxide solution and the resulting suspension was thoroughly mixed then allowed to stand at ambient temperature (22° C.) for 15 hours. Then 1 liter of ethyl acetate and 100 mL of concentrated hydrochloric acid were added and the suspension mixed. The ethyl acetate phase was separated and the fibre suspension re-extracted with a further 1 liter of ethyl acetate. The combined organic solvent phases were dried (Na$_2$SO$_4$) and evaporated to dryness to yield a thick oil. Repeated washing of this oil with n-hexane gave a pale yellow solid comprising 33% ferulic acid and 2.9% coumaric acid.

(b) Use of sodium bicarbonate: to 10 g maize fibre containing 1.75%w/w ferulic acid (FA) and 0.1%w/w coumaric acid (CA) was added 100 ml 0.5 m sodium bicarbonate solution in a 250 ml conical flask. The resulting suspension was heated and mixed at 85° C. using a hot plate stirrer apparatus. The release of ferulic acid and coumaric acid into solution was monitored over time using hplc.

Ferulic acid and coumaric acid yields were as follows: 60 min., FA 20 mg, CA 1.6 mg; 245 min., FA 100 mg, CA 4.3 mg; 315 min, FA 127 mg, CA 5.6 mg; 365 min., FA 126 mg, CA 6.2 mg. Yields at 365 min are equivalent to 72% and 62% release of available ferulic acid and coumaric acid respectively.

The maize suspension was coarse filtered by pressing through a mesh bag, the recovered solids washed with 10 ml deionised water and the filtrates combined prior to centrifugation (4,000×g, 15 min). The pH of the supernatant was adjusted to pH 2.5 with concentrated hydrochloric acid followed by extraction with ethyl acetate (3×100 ml). Evaporation of the combined ethyl acetate layers to dryness yielded 216 mg of yellow/orange solid material comprising 41% ferulic acid and 2.7% coumaric acid.

In the following examples (c) and (d), the production of ferulic acid and coumaric acid from maize fibre was effected by a two step process. Firstly, acid hydrolysis of the fibre was achieved by heating with citric acid solutions, supplied as either a defined quantity of citric acid dissolved in water or as the juice from freshly squeezed lemon or lime fruit. Secondly, the hydrolysis of solubilised cinnamate sugar esters was achieved by the addition of a hydrolytic enzyme preparation yielding ferulic and coumaric acids.

(c) Maize fibre (20 g) was mixed with 100 ml of citric acid solution (2%) in 250 ml conical flask and heated at 126° C. for 1 hour. The pH of the maize suspension was raised to pH 5.0 by the addition of 10M sodium hydroxide solution with vigorous mixing. An enzyme preparation (40 mg, Hemicellulase, Amano) was added to the suspension and the whole incubated at 50° C. for 46.5 hours with mixing at 200 rpm. The release of ferulic acid was monitored by hplc as described above. After 1.5 hours incubation a total of 51 mg ferulic acid was present in solution, after 46.5 hours this amount had risen to 220 mg.

(d) Maize fibre (200 g) was mixed with-1 liter citric acid solution (2%) in a 2 L conical flask and heated at 126° C. for 1 hour. The maize suspension was separated into insoluble solids and a liquor fraction using a wine press. First pressing yielded approximately 800 ml liquor; the recovered solids were washed with a further 200 ml of water and pressed again to give approximately 1 liter of combined liquor fractions. The pH of the maize liquor was raised to pH 7.0 by the addition of 10M sodium hydroxide with vigorous mixing. An enzyme preparation (Biofeed Plus L, 2 ml, Novo Nordisk) was added to the liquor and the whole incubated at 60° C. for 7.5 hours with mixing at 160 rpm. The release of ferulic acid and coumaric acid was monitored by hplc as described above. After 7.5 hour incubation 1.6 gL$^{-1}$ ferulic acid and 0.1 gL$^{-1}$ p-coumaric acid were detected in solution. Both cinnamic acids were recovered from aqueous solution by extraction into ethyl acetate as described below, followed by either, base extraction of the solvent to yield the cinnamate sodium salt, or evaporation of the solvent to dryness to yield the cinnamate free acid.

Maize liquor (1 L) was brought to pH 3 by the addition of concentrated hydrochloric acid and filtered through diatomaceous earth to remove insoluble material. The filtrate was extracted twice with 300 ml of ethyl acetate and the solvent extracts combined. Evaporation of solvent to dryness yielded 2.6 g of orange solid comprising 1.39 g ferulic acid and 0.1 g coumaric acid, 53.5% and 3.8% purity respectively. In order to recover the cinnamates as their sodium salts, the ethyl acetate was continuously pumped over 10M sodium hydroxide solution (10 ml) combined with vigorous mixing of the aqueous phase. This was continued until all but trace quantities of cinnamate had been recovered into the aqueous phase (approx. 2 hrs). The aqueous phase was dried under vacuum at 45° C. to yield 11.5 g of cream solid material comprising 1.3 g ferulic acid and 0.1 g coumaric acid, 11.3% and 0.87% purity respectively.

e) Conversion of citric acid treated maize fibre suspension to a digested pulp containing ferulic acid and vanillic acid 4 g maize fibre containing ca 1.75% w/w ferulic acid and 20 ml 2% w/v citric acid solution were added to each of three 50 ml conical flasks and the whole autoclaved at 126° C. for 55 minutes. After cooling the pH of the treated suspension was adjusted to pH 6.0 using 10M sodium hydroxide solution. Flasks were inoculated with spores of either Zyl 714 (IMI 379895) *Aspergillus flavus*, Zyl 759 (IMI 379904) *Aspergillus niger* or *P. chrysogenum* Zyl 860 (IMI 379900) and incubated at 30° C., shaking at 250 rpm on an orbital mixer. Flasks were assayed by hplc for the hydrolytic product ferulic acid, and for the ferulic acid side chain cleavage product vanillin acid.

After 89 hours incubation the concentrations of ferulic acid and vanillic acid in solution for the *P. chrysogenum* experiment were ferulic acid, undetectable; and vanillic acid, 1.35 g/L.

Concentrations of ferulic acid and vanillic acid in solution for *Aspergillus flavus, Aspergillus niger* respectively after 5 days incubation were 1 g/L ferulic acid and 0.3 g/l vanillic acid; undetectable ferulic acid and 1.2 g/L vanillic acid.

All three fungi reduced the maize fibre suspension to a digested pulp and the fibre fragments to fine solids.

f) Pilot scale processing of maize fibre for release of ferulic acid 3 batches of 10 kg maize fibre were each suspended in 50 L of 2% w/v aqueous citric acid solution. Batch 1 and 2 were heated to 126° for 1 hour and then rapid cooled to 80° C. using an Agemore swept surface heating/mixing vessel. The solids were then separated from the liquor using a Vigo 72 L winepress, and the solids washed with water to restore the starting volume.

Batch 1 and 2 combined generated 100 L of liquor. A sample of this liquor was treated by base hydrolysis to release the available ferulic acid and analysed by hplc, the ferulic acid concentration was 1.5 gL$^{-1}$.

The third batch was heated to 134° C. for 15 minutes, rapid cooled to 80° C., and pressed using the same apparatus as batches 1 and 2, however the solids were not washed with water after the first pressing. This batch generated 44.5 L of liquor. A sample of this liquor was treated by base hydrolysis to release the available ferulic acid and analysed by hplc, the ferulic acid concentration was 1.12 gL$^{-1}$.

All three batches of liquor were then combined to give 145 L and the concentration of suspended solids measured as 10.5% w/v by refractometry, the pH was measured as pH 3.4. The liquor was then concentrated using a Junior rising/falling plate evaporator at 60° C. 19.5 L of liquor was obtained, the suspended solids level was determined, by refractometry, to be 50%. A sample of this liquor was treated by base hydrolysis to release the available ferulic acid and analysed by hplc, the ferulic acid concentration was 8.0 $gL^{-1}$.

The concentrated liquor was then transferred to a 70 L Biolafitte fermenter and diluted with water to give a total volume of 33 L. The pH of the liquor was adjusted from pH 3.0 to pH 6.0 with 2.5 L 32% w/v sodium hydroxide solution. The liquor was then heated to 45° C. An enzyme, hemicellulase (Amano), was added at a concentration of 0.8 $gL^{-1}$, and the mixture incubated with stirring for 30 hours. After the enzyme treatment, the liquor was analysed by hplc, the ferulic acid concentration was 3.5 $gL^{-1}$.

The pH of the liquor was lowered to pH 3.0 with 82.5% w/v phosphoric acid and the suspended solids removed by centrifugation using a Carr Powerfuge. The ferulic acid was then extracted from the liquor using 50 L of butyl acetate (in two batches of 25 L). The butyl acetate was overlaid on the liquor and mixed gently in the fermenter, until the concentration of ferulic acid in the butyl acetate layer stopped increasing. 48 L of butyl acetate were recovered once the extraction was complete. Analysis of the butyl acetate by hplc gave the ferulic acid concentration as 2.64 $gL^{-1}$.

g) Pilot scale processing of sugar beet for release of ferulic acid 40 kg Fibrex sugar beet fibre was suspended in 200 L water overnight. This suspension was then heated to 134° C. for 30 minutes and then rapid cooled to 80° C. (cooling time was 10 minutes) using an Agemore swept surface heating/mixing vessel. The solids were then separated from the liquor using a Vigo 72 L winepress, and the solids washed with water to restore the starting volume.

200 L of liquor was obtained, the pH was measured as pH 4.0, the suspended solids level was determined, by refractometry, to be 9.5% w/v. A sample of this liquor was treated by base hydrolysis to release the available ferulic acid and analysed by hplc, the ferulic acid concentration was 1.03 $gL^{-1}$.

The liquor obtained was then concentrated using a Junior rising/falling plate evaporator at 60° C. 31 L of liquor was obtained, the suspended solids level was determined, by refractometry, to be 50% w/v. A sample of this liquor was treated by base hydrolysis to release the available ferulic and analysed by hplc, the ferulic acid concentration was 5.2 $gL^{-1}$.

The liquor was then transferred to a 70 L Biolafitte fermenter and heated to 60°. The pH was adjusted to, and controlled at, pH 6.5 with 20% w/v phosphoric acid. An enzyme, Pentopan BG 500 (Novo Nordisk), was added at a concentration of 1.8 $gL^{-1}$, and the mixture incubated, with stirring, for 24 hours. After the enzyme treatment, the liquor was analysed by hplc, the ferulic acid concentration was 2.55 $gL^{-1}$.

The pH of the liquor was lowered to pH 3.0 with 82.5% w/v phosphoric acid and the suspended solids removed by centrifugation using a Carr Powerfuge. The ferulic acid was then extracted from the liquor using 35 L of butyl acetate (in three batches, 2×15 L, 1×5 L). The butyl acetate was overlaid on the liquor and mixed gently in the fermenter, until the concentration of ferulic acid in the butyl acetate layer stopped increasing. 32 L of butyl acetate were recovered once the extraction was complete. Analysis of the butyl acetate by hplc gave the ferulic acid concentration as 2.10 $gL^{-1}$.

The ferulic acid was then extracted from the butyl acetate by base extraction. The butyl acetate was pumped through 50 ml of deionised water in a 500 ml Duran bottle. The water was maintained at pH 9.0 using a Metrohm pH Stat titrating 10M sodium hydroxide and mixed using a magnetic stirrer plate and stirrer bar. Once it had passed through the aqueous phase, the butyl acetate was pumped back into the bulk solvent volume. This arrangement extracts the ferulic acid from the solvent phase and concentrates it in the pH 9.0 aqueous phase. The aqueous phase eventually became saturated with ferulic acid and a precipitate was formed which was recovered by filtration under vacuum through Whatman no.41 filter papers. These solids were dried overnight at 50° C. in a drying oven. The first batch of solids obtained by this method weighed 34 g and contained 24 g ferulic acid by hplc analysis. The second batch of solids weighed 18 g and contained 8 g ferulic acid by hplc analysis.

h) Pilot scale processing of maize fibre for release of ferulic acid by base hydrolysis 1 tonne of maize fibre was suspended in 10,000 L of water containing 600 Kg 30.5% sodium hydroxide. This was then heated to 50° C. in a 15 $m^3$ stainless steel jacketed vessel and mixed for 8 hours. The pH of this suspension was measured as pH 11.8.

The bulk solids were then removed using a scroll decanter, and the liquor obtained transferred to a storage vessel. The pH of the liquor was then adjusted to pH 6.0 with 160 Kg 75% w/v phosphoric acid.

The liquor was then concentrated using an APV evaporator, which gave a final product of 2.5 tonnes. After concentration, the pH of the liquor was lowered to pH 3.0 with 180 Kg 75% w/v phosphoric acid. A sample of this material was removed and analysed for ferulic acid by hplc, the ferulic acid concentration was 2.1 $gKg^{-1}$.

i) Repeat use of citric acid solutions for extraction of ferulic acid from maize fibre 20 g of Citric acid was dissolved in 1 liter of RO water, pH was measured as pH 2.20. 200 g of maize fibre (supplied by Staley) was added to the citric acid solution and then autoclaved at 121° C. for 60 minutes. The solids were then separated from the liquor using a Vigo bench wine press whilst the suspension was still at 80° C. 800 ml of liquor was recovered from the initial pressing. The retained solids were then washed with 200 ml RO water, and pressed a second time. 220 ml of liquor was recovered from the second pressing. The liquor obtained from both pressings were added together to give a total volume of 1.02 L. The pH of the liquor was measured as pH 2.32.

A sample of liquor was treated by base hydrolysis to release the available ferulic acid and analysed by hplc, the ferulic acid concentration was 2.49 $gL^{-1}$. This represents a yield of 1.24% w/w ferulic acid from maize fibre.

The pH of the liquor was returned to pH 2.20 using 2.37 g of citric acid. A fresh 200 g of maize fibre (supplied by Staley) was added to the liquor and then autoclaved at 121° C. for 60 minutes. The suspension was treated as described above, 730 ml was recovered from the first pressing, the solids were washed with 270 ml of RO water and pressed again, 320 ml was recovered from the second pressing. The liquors obtained from both pressings were added together to give a total volume of 1.05 L. The pH of the liquor was measured as pH 2.58.

A sample of liquor was treated by base hydrolysis to release the available ferulic acid and analysed by hplc, the ferulic acid concentration was 3.13 $gL^{-1}$. This represents a yield of 0.82% w/w ferulic acid from maize fibre.

EXAMPLE 1B

Biotransformation of Product Mixtures

A seed stage culture of *Rhodotorula glutinis* (Zyl 717) was grown for 24 hours at 30° C. with shaking at 200 rpm in a 250 mL shake flask containing 50 mL of minimal medium (containing 2 g/l $KH_2PO_4$; 0.2 g/l NaCl; 0.22 g/l $MgSO_4$; 0.015 g/l $CaCl_2$; 1 ml/l trace elements solution; 10 ml/l vitamins solution; 4 g/l yeast extract; 4 g/l glucose). This culture was used to inoculate (2%) a 250 mL shake flask containing 50 mL of the same medium to which was added 300 mg of the maize extract produced in example (a) above. This gave an equivalent to 2 $gL^{-1}$ ferulic acid and 0.18 $gL^{-1}$ coumaric acid substrates. The mixture was agitated at 500 rpm at 300 with a dissolved oxygen level of 60% of saturation. Substrate and product concentrations were measured by hplc as the following: 16 hours, ferulic acid 0.68 $gL^{-1}$, vanillic acid 1 g $L^{-1}$, coumaric acid 0.08 $gL^{-1}$, 4-hydroxybenzoic acid 0.05 $gL^{-1}$, 3,4-dihydroxybenzoic acid 0.02 $gL^{-1}$; 18 hours, ferulic acid 0.14 $gL^{-1}$, vanillic acid 1.54 $gL^{-1}$, coumaric acid 0.035 $gL^{-1}$, 4-hydroxybenzoic acid 0.08 $gL^{-1}$, 3,4-dihydroxybenzoic acid 0.05 $gL^{-1}$.

The product mixture can undergo further biotransformation, e.g. with reduction of —$CO_2H$ groups to —$CH_2OH$ and/or —CHO e.g. using *Zygorhynchus moelleri* or *Micromucor isabellinus* (see below). Thus the vanillic acid may be converted into a mixture of vanillin and vanillyl alcohol, in variable proportions. Likewise the 4-hydroxybenzoic acid may be converted into a mixture of 4-hydroxybenzaldehyde and 4-hydroxybenzyl alcohol. The minor acid components may undergo corresponding reductions. Thus the end product is a complex mixture of odoriferous compounds, principally of vanilla type. The proportion of aldehydes (such as vanillin) can be increased by biotransformation of the alcohols in the mixture, e.g. using *Brevundimonas vesicularis*.

EXAMPLE 1C

Production of Vanillic Acid From Maize Fibre

Maize fibre (1 kg) was subjected to citric acid hydrolysis (5 L, 2% solution) followed by pressing and washing of the maize solids to give approximately 5 liters of maize liquor as described in (c) above. The pH of the liquor was adjusted to pH5.8 using 10M sodium hydroxide. A 2 L aliquot of the above liquor was transferred into a 5 L working volume fermenter and heated to 100° C. for 1 minute. The remaining liquor was also heat-treated and stored separately. The fermenter was inoculated with 200 ml of a culture of *Penicillium chrysogenum* (Zyl 860) grown on pH5.8 maize liquor for 30 hours in a 1 liter conical flask (28° C. shaking at 250 rpm). The fermenter contents were grown for 15 hours at 28° C. while controlling the dissolved oxygen concentration at 30% of saturation. The pH of the culture was not controlled but remained unchanged throughout the incubation period. After 15 hours the volume of the fermenter contents was increased initially to 3.5 L and then to 5 L after a further 7 hours incubation. Incubation was continued as described previously for a further 3 days after which time the fermenter contents were assayed by hplc as described above. The maize liquor was shown to contain 1.2 $gl^{-1}$ vanillic acid and only a trace quantity of ferulic acid. Fungal biomass was separated from the maize liquor by a single pressing of the fermenter contents through a wine press to give a clarified aqueous product.

Whereas *P.chrysogenum* (Zyl 860) is the currently preferred strain, *Aspergillus flavus* (Zyl 714) and *A. niger* (Zyl 759) are also usable.

Vanillic acid can be recovered from aqueous solution by extraction into ethyl acetate followed by either evaporation of the solvent to dryness or by precipitation of vanillic acid from the solvent by the addition of hexane. For example, a culture broth (900 ml) comprising 567 mg vanillic acid was acidified to pH 3.0 and extracted three times with ethyl acetate (1×400 ml, 2×200 ml). The solvent extracts were combined, assayed by hplc as described above and found to contain 485 mg vanillic acid (86% recovery).

An aliquot (200 ml) was taken from the combined ethyl acetate extracts and the volume reduced to approximately 10 ml by evaporation. Hexane (40 ml) was added slowly to this concentrated extract, accompanied by constant mixing, the precipitated material was recovered by filtration and dried to yield 140 mg of pale yellow solid comprising 115 mg vanillic acid (82% purity). Recovery from the solvent was 88%, therefore, giving an overall recovery of 76% from the original culture broth.

EXAMPLE 1D

Production of Vanillin From Maize Fibre

The nutrient content of the clarified liquor from Example 1C was enhanced for growth of Micromucor isabellinus by the addition of nutrients as described in Example 4 below. No further vanillic acid was added to the liquor. A culture of *Micromucor isabellinus* (Zyl 849) was grown at 30° C. for 3 days on pH 5.8 maize liquor (described in Example 1C) solidified with 1.5% agar. This culture was used to inoculate 20 ml of the enhanced clarified liquor described above contained in a 100 ml conical flask. The flask contents were incubated at 30° C. with shaking at 250 rpm for 24 hours, prior to being used to inoculate (2.5%) a second identical flask. Incubation conditions were as described previously. The concentrations of vanillic acid and vanillin in solution throughout the process were assayed by hplc as described above. After 24 hours incubation the pH of the liquor was slowly reduced over approximately 1.5 hours from pH5.2 to pH3.7. After 2.25 hours post onset of the pH reduction, 0.02 $gL^{-1}$ vanillin was detected in solution. After 4.5 hours the vanillin concentration had increased to 0.12 $gL^{-1}$. At 7.5 hours the vanillin and vanillic acid concentrations were 0.275 $gL^{-1}$ and 0.81 $gL^{-1}$ respectively. After 13 hours incubation the vanillic acid concentration had decreased to 0.45 $gL^{-1}$ and the concentration of vanillin had reached a maximum at 0.35 $gL^{-1}$.

B) Vanillin From Vanillic Acid Via Vanillyl Alcohol

'One pot' bioconversions of vanillic acid to vanillin are known, but they generally show low yields and low conversion rates and/or low product concentrations (e.g. EP 453368, FR 2724394). We have found that *Zygorhynchus moelleri* can be used to produce very high concentrations of vanillyl alcohol (e.g. >5 g/l) from vanillic acid. Vanillyl alcohol can be efficiently oxidised to vanillin, e.g. by means of *Brevundimonas vesicularis*.

EXAMPLE 2

Vanillyl Alcohol From Vanillic Acid

A culture of *Zygorhynchus moelleri* (Zyl 851) grown on yeast malt agar was used to inoculate a 250 mL starter culture flask containing 50 mL medium, (20 g glucose; 5 g $(NH_4)_2SO_4$; 2 g NaCl; $MgSO_4$ 0.22 g/L; $CaCl_2$ 0.015 g/L, 10 mL; trace element solution, 1 mL; vitamins solution 10 mL; made up to 1 liter with pH6.0 phosphate buffer, 0.2M), containing 2 g/L vanillic acid, which was incubated at 30° C. with shaking at 200 rpm for 24 hours. This starter culture was added to 5 liters of the same medium in a fermenter except that the medium components were dissolved in deionised water and also containing 2 g/L vanillic acid. This was stirred at pH 5.2, (30° C.) for 24 hours after which the pH was altered to 3.5 over 1 hour, and the temperature kept at 30° C. Dissolved oxygen was maintained at 70% of saturation throughout the process. Assay was by hplc. Prior to the pH being allowed to drop (at the 24 hour stage), the amount of vanillic acid present in the system had not dropped and no products were seen. As the reaction is proceeded, various amounts of substrate and nutrients were added as follows: 31.75 hours, 10 g vanillic acid and 25 g glucose; 47.5 hours, 50 g glucose; 55 hours, 20 g vanillic acid. Products were measured as being the following: 31.75 hours; vanillic acid, 0.26 g/L, vanillyl alcohol, 0.3 g/L; 47.5 hours, vanillic acid, 1.17 g/L, vanillin, 0.1 g/L, vanillyl alcohol, 2.38 g/L; 55 hours, vanillic acid, 0.64 g/L, vanillin, 0.06 g/L, vanillyl alcohol, 3.5 g/L; 5 days, vanillic acid, 1.21 g/L, vanillin, 0.05 g/L, vanillyl alcohol, 6.6 g/L; after this stage no further product accumulation was observed. It is also evident that at pH 5.2 no substrate was converted into any products and the bioconversion only started when the pH was allowed to drop to pH 3.5.

EXAMPLE 3

Vanillin From Vanillyl Alcohol

Sterile nutrient broth (No 2) (50 mL) in a 250 mL shake flask was inoculated with *Brevundimonas vesicularis* (Zyl 295) and incubated at 30° C. with shaking at 200 rpm. After 24 hours the addition of 50 mg of vanillyl alcohol was followed by the flask being monitored regularly by hplc for both vanillyl alcohol and vanillin. Up to 71 hours post inoculation the amount of vanillyl alcohol decreased to around 10% of the original level and the amount of vanillin increased to approximately 90% molar conversion from substrate. Identification of the structure of the product was confirmed by nmr spectroscopy.

If the vanillyl alcohol was added at the time of inoculation of the flask then the amount of substrate did not start to decrease until after 16 hours incubation when vanillin was first detected. The overall conversions closely followed those seen when substrate was added after 24 hours.

C) Vanillin From Vanilic Acid

As mentioned above, the biotransformation of vanillic acid into vanillin is known, but the yields of known methods are poor, making them unattractive in commercial terms. FR-A-2724394 discloses a process, using a basidiomycete, which gives fairly good yields and conversion rates in percentage terms, but whose absolute yields are low. The highest yield of vanillin produced in an example is 628 mg/l.

We have found strains capable of affording vanillin at greater than 1 g/l and usable in continuous production systems. Preferred microorganisms are strains of *Micromucor isabellinus* and *Aspergillus fumigatus*.

EXAMPLE 4

Production of Vanillin by *M. isabellinus*

(a) A culture of *Micromucor isabellinus* (Zyl 849) grown on yeast malt agar was used to inoculate a 250 mL starter culture flask containing 50 mL medium (15 g glucose; 5 g $(NH_4)_2SO_4$; 2 g $K_2HPO_4$; 0.2 g NaCl; 0.2 g $MgSO_4$; 0.015 g $CaCl_2$, trace element solution, 1 mL; vitamins solution 10 mL; made up to 1 liter with deionised water) containing 2 g/L vanillic acid which was incubated at 30° C. with shaking at 200 rpm for 16.5 hours. This starter culture was added to 5 liters of the same medium in a fermenter with vanillic acid added to a concentration of 1.5 $gL^{-1}$. The fermenter contents were stirred at 30° C. with the dissolved oxygen concentration being maintained at 70% of saturation throughout the process. Assay was by hplc as described above. As the reaction proceeded, additional amounts of vanillic acid were added as follows: 22.5 hours, 2.5 g; 24 hours, 2.5 g; 25.75 hours, 1 g; 26.5 hours, 1 g; 27.5 hours, 1 g; 31 hours, 2.5 g. Substrate and product concentrations were measured as being the following: 22.5 hours, vanillic acid 0.6 $gL^{-1}$; vanillin 0.84 $gL^{-1}$; 24 hours, vanillic acid 1.36 $gL^{-1}$; vanillin 0.96 $gL^{-1}$; 25.75 hours, vanillic acid 1.15 $gL^{-1}$; vanillin 1.1 $gL^{-1}$; 26.5 hours, vanillic acid 1.27 $gL^{-1}$; vanillin 1.17 $gL^{-1}$; 27.5 hours, vanillic acid 1.43 $gL^{-1}$; vanillin 1.33 $gL^{-1}$; 31 hours, vanillic acid 1.16 $gL^{-1}$; vanillin 1.6 $gL^{-1}$; 46 5 hours, vanillic acid 1.58 $gL^{-1}$; vanillin 1.70 $gL^{-1}$.

(b) A culture of *Micromucor isabellinus* (Zyl 849) grown on yeast malt agar was used to inoculate a 500 mL starter culture flask containing 100 mL medium (15 g glucose; 5 g $(NH_4)_2SO_4$; 2 g $K_2HPO_4$; 0.2 g NaCl; 0.2 g $MgSO_4$; 0.015 g $CaCl_2$, trace element solution, 1 mL; vitamins solution 10 mL; made up to 1 liter with pH 6.0 phosphate buffer (0.2M)) containing 2 g/L vanillic acid which was incubated at 30° C. with shaking at 200 rpm for 24 hours. This starter culture was added to 5 liters of the same medium in a fermenter with the medium components made up to 1 liter with deionised water and vanillic acid added to a concentration of 1.5 $gL^{-1}$, immediately prior to inoculation. The fermenter contents were stirred at 30° C. for 18 hours with the pH of the medium being maintained at pH 5.2 by the addition of 5M sodium hydroxide solution. After this time the medium pH was gradually reduced to 3.7 over 45 minutes by the addition of 5M HCl and temperature was maintained at 30° C. Dissolved oxygen concentration was maintained at 70% of saturation throughout the process. Assay was by hplc as described above. Prior to the pH being allowed to drop at the 18 hour stage, the amount of vanillic acid in the system was measured at 1.48 $gL^{-1}$; vanillin was detected in solution at 0.02 gL-l. As the reaction proceeded various amounts of vanillic acid or glucose were added as follows: 19.25 hours, 50 g glucose; 20.25 hours, 3 g vanillic acid; 21.5 hours, 4 g vanillic acid; 23 hours, 4 g vanillic acid. Substrate and product concentrations were measured as being: 19.25 hours, vanillic acid 1.5 $gL^{-1}$, vanillin 0.1 $gL^{-1}$;: 20.25 hours, vanillic acid 1.16 $gL^{-1}$, vanillin 0.36 $gL^{-1}$;: 21.5 hours, vanillic acid 1.07 $gL^{-1}$, vanillin 0.74 $gL^{-1}$;: 23 hours, vanillic acid 1.06 $gL^{-1}$, vanillin 1.22 $gL^{-1}$;: 26 hours, vanillic acid 0.83 $gL^{-1}$, vanillin 1.96 $gL^{-1}$.

EXAMPLE 5

Production of Vanillin by *A. fumigatus*

A spore suspension of *Aspergillus fumigatus* (Zyl 747) was used to inoculate 5 liters of a minimal medium (ingredients described in Example 4(a), except for the addition of 3 $gL^{-1}$ vanillic acid rather than 1.5 $gL^{-1}$). The fermenter contents were stirred without pH control at 30° C. with the dissolved oxygen concentration being maintained at 60% of saturation. Assay was by hplc as described above. Substrate and product concentrations in the culture broth were as follows: 16 hours, vanillin 0.015 $gL^{-1}$; 24 hours, vanillin 0.075 $gL^{-1}$; 40 hours, vanillin 0.69 $gL^{-1}$; 47 hours, vanillin 0.91 $gL^{-1}$; 48.5 hours, 0.98 $gL^{-1}$; 53.5 hours 1.02 $gL^{-1}$; 112 hours, vanillic acid 1.32 $gL^{-1}$, vanillin 1.09 $gL^{-1}$ D) Vanillin From Ferulic Acid

EXAMPLE 6

Conversion of Ferulic Acid to Vanillin by Zyl 581 an NTG Derived Mutant of Zyl503

Background

ZYL503 converts ferulic acid (FA) to vanillin acid (VA) via the intermediate vanillin. The rate-limiting step in this reaction is FA to vanillin, therefore accumulation of vanillin in culture media is not observed. Based on the NTG mutation method described below a ZYL503 mutant has been produced that accumulates vanillin in culture media when supplied with FA.

(a) NTG Mutagenesis of ZYL503

ZYL503 was grown to mid-exponential phase in 10 ml nutrient broth, harvested, washed once in 100 mM sodium citrate buffer (pH 5.5), resuspended in 10 ml of this buffer containing 0.1 $gL^{-1}$ NTG, and incubated at room temperature. At five minute intervals 0.5 ml aliquots were taken, washed twice in 50 mM potassium phosphate buffer, and resuspended in 1 ml of this buffer. These samples were then diluted in 50 mM phosphate buffer and spread onto a minimal medium agar (pH7, 0.4M phosphate buffered), that contained 20 $gl^{-1}$ glucose or 1 $gl^{-1}$ vanillin plus 2 $gl^{-1}$ yeast extract and 2 $gl^{-1}$ ferulic acid. Plates were incubated at 30° C. for 24–48 h. Resultant colonies unable to grow on vanillin plates were selected. Zyl 581 was obtained based on this procedure.

(b) Conversion of Commercial Ferulic Acid (Free Acid) to Vanillin by Zyl 581

A preculture of Zyl 581 was grown in a 250 ml shake flask containing 50 ml minimal medium ($gl^{-1}$: $(NH_4)_2SO_4$, 5; $K_2HPO_4$, 2; NaCl, 0.2; Yeast extract, 0.2, glucose, 20:10 ml of a solution containing 0.1 M $MgSO_4$/0.01M $CaCl_2$; 10 ml vitamin solution and 1 ml trace elements solution at 200 rpm, 30° C. for 24 h. This culture was then used to inoculate a bioreactor filled with 1.2 l of the same medium with pH control at 8.0 using 2M NaOH, oxygen control at 70% with a stirrer speed cascade of 100–400 rpm air flow 1.3 vvm. Prior to inoculation 2 $gl^{-1}$ ferulic acid (Lancaster, 99%) was added as the fermentation proceeded as indicated in the table below. An identical reactor was also set up with pH control at 8.5. Reaction products were quantified by HPLC.

pH 8.0

| Time (h) | FA (g $l^{-1}$) | VA (g $l^{-1}$) | Vanillin (g $l^{-1}$) | FA added (g $l^{-1}$) |
|---|---|---|---|---|
| 0 | 1.8881 | 0.000 | 0.000 | |
| 19.7 | 0.616 | 0.298 | 0.545 | |
| 21.2 | | | | 1.380 |
| 21.7 | 1.953 | 0.433 | 0.460 | |
| 23.7 | 1.865 | 0.347 | 0.619 | |
| 25.7 | 1.806 | 0.798 | 0.260 | |
| 27.7 | 1.786 | 0.912 | 0.182 | |
| 43.4 | 1.105 | 1.039 | 0.278 | |
| 48.0 | 0.387 | 1.245 | 0.577 | | pH 8.5

| Time (h) | FA (g $l^{-1}$) | VA (g $l^{-1}$) | Vanillin (g $l^{-1}$) | FA added (g $l^{-1}$) |
|---|---|---|---|---|
| 0 | 1.891 | 0.000 | 0.000 | |
| 19.7 | 0.520 | 0.000 | 0.545 | |
| 21.2 | | | | 1.450 |
| 21.7 | 1.802 | 0.000 | 1.161 | |
| 23.7 | 1.380 | 0.000 | 1.418 | |
| 25.7 | 1.074 | 0.025 | 1.475 | |
| 26.0 | | | | 0.970 |
| 27.7 | 1.829 | 0.038 | 1.521 | |
| 43.4 | 0.424 | 0.083 | 2.247 | |
| 44.8 | | | | 1.540 |
| 48.0 | 1.871 | 0.115 | 2.193 | |

At pH8 vanillic acid was the predominant transformation product from ferulic acid while at pH 8.5 vanillin was the predominant product. After 43 h at pH 8.5 the vanillin concentration was 2.247 $gl^{-1}$ a molar yield of 73% for the ferulic acid consumed.

(c) Conversion of Sugar Beet Derived Ferulic Acid (Sodium Salt) to Vanillin by Zyl581

Ferulic acid obtained from Pentopan 500BG treated sugar beet liquor was extracted with butyl acetate, then back extracted into base to give the ferulic acid sodium salt (70.8% w/w ferulic acid as free acid).

Zyl581 was grown in a bioreactor as described above at pH 8.5 except that prior to inoculation 5.65 g/l sugar beet ferulic acid extract was added (4 $gl^{-1}$ available ferulic acid present as sodium salt). After 40 h the ferulic acid concentration in the reactor was 0.05 g/l, vanillin acid 0.21 g/l and vanillin 1.69 g/l. This represents a molar yield for vanillin of 54%. 72% of the ferulic acid added could be accounted for as vanillic acid, vanillin or remaining ferulic acid.

(d) Recovery of Vanillin From Spent Culture Broth

The culture broth from the Zyl581 fermentation was taken, cells removed by centrifugation, the broth adjusted to pH 7.5, overlaid with an equal volume of butyl acetate and stirred overnight. The butyl acetate was evaporated under vacuum and the resultant solid washed with 10 ml hexane, recovered by filtration and dried at 40° C. overnight. 400 mg of the extracted solid from the Zyl581 fermentation (95% w/w vanillin by HPLC), was purified using the following procedure. The product was dissolved in 10 ml diethyl ether to which 40 mg of silica (70–200 μm) was added. The ether was evaporated leaving the solid adsorbed to the silica. The silica was washed with 500 ml of a 2% (v/v) solution of ethyl acetate in petroleum ether (60–80 fraction). This solution was filtered through a glass sinter and evaporated under vacuum to yield a white amorphous solid containing greater than 99% w/w vanillin (277 mg).

E) In Situ Product Removal ("ISPR")

The principle involves carrying out a biotransformation in an aqueous phase which is in contact with, or is contacted with, an immiscible phase into which a product can pass (exclusively or preferentially). Possible advantages include a) the protection of a product from further reaction in the aqueous phase; b) avoidance of inhibition of product formation by a microorganism by high product concentrations; c) enabling equilibrium reactions to convert a larger proportion of starting material into product; and d) ease of isolation of products. Furthermore ISPR can assist in the development of continuous systems.

ISPR is readily applied to systems where a polar substrate (e.g. a carboxylic acid such as ferulic or vanillic acid) is converted into a less polar product, which will be preferentially extracted by a nonpolar solvent such as a plant oil material, preferably food grade. Polar byproducts will also tend to stay in the aqueous phase.

Examples 7 and 8 correspond to Examples 4 and 5 but make use of ISPR.

Depending on the system, the immiscible phase may contact the aqueous phase while biotransformation is proceeding therein, or it may contact portions of the aqueous phase which have been withdrawn (temporarily) from the bioreactor. The withdrawn phase may be treated (e.g. by adjustment of pH) to facilitate extraction by the immiscible phase.

EXAMPLE 7

Production of Vanillin by M. isabellinus With ISPR

A 5 liter culture of *Micromucor isabellinus* (Zyl 849) was grown in a fermenter as described in Example 4b. The fermenter contents were stirred at 30° C. for 20 hours with the pH of the medium maintained at 5.2 by the addition of 5M sodium hydroxide solution. After this time the medium pH was gradually reduced to 3.8 over 45 minutes by the addition of 5M HCl and was maintained at this pH thereafter; temperature was maintained at 30° C. Dissolved oxygen concentration was maintained at 70% of saturation throughout the process. Assay was by hplc as described above. The progress of the reaction was monitored until the concentration of vanillin in the culture broth reached 0.96 gL.$^{-1}$. Throughout this period vanillic acid was added to the medium to maintain a concentration of 1.5 gL.$^{-1}$. At this time an external vanillin extraction system was activated as follows: culture medium was continuously pumped from the fermenter through a filtration device such that the biomass was retained within the fermenter; culture medium exiting the fermenter was heated to 60° C. and adjusted to pH 6.5 by the addition of 10M sodium hydroxide solution; this medium was fed into an extraction vessel containing 5 liters of sunflower oil; the aqueous phase (maintained at 1 liter volume) and the oil phase were stirred vigorously by the use of an overhead stirrer to effect continuous selective extraction of vanillin from the culture medium into the oil phase; vanillic acid did not extract into the oil and remained entirely in the aqueous phase; this aqueous phase was continually pumped back into the fermenter. Throughout the process, the volume in the fermenter and the volume in the extraction vessel remained relatively constant. The concentration of vanillic acid in the fermenter was maintained at approximately 1.5 gL.$^{-1}$ and the concentration of vanillin in the fermenter was maintained at a maximum of 1.5 gL.$^{-1}$. Using this continuous external extraction facility the 5 liter culture of *Micromucor isabellinus* produced 18.9 g vanillin over an operational period of approximately 20 hours. Vanillin can be recovered from sunflower oil by extraction into water, or alcohol, e.g. methanol or ethanol, or into an alcohol/water mixture. A suitable mixed solvent is 80% ethanol and 20% water. After evaporation of the extraction solvent, vanillin can be further purified by traditional techniques such as recrystallisation, sublimation etc.

EXAMPLE 8

Production of Vanillin by *A. fumigatus* With ISPR

A sterile glass column (60 mL volume) packed with a stainless steel support was filled with a minimal medium (ingredients described in Example 4) containing 2 gL$^{-1}$ vanillic acid and inoculated with spores of *Aspergillus fumigatus* (Zyl 747). Air was pumped into the base of the column in order to aerate the system and effect efficient mixing. The column was allowed to stand at room temperature (22° C.) for 70 hours. After this time substantial growth of the fungus had occurred and all had adhered to the stainless steel support material. The concentration of vanillin in solution was measured as 0.65 gL$^{-1}$. Maintaining aeration as described above, the contents of the column were continuously pumped out of the column into a separate extraction vessel containing 500 mL sunflower oil and 200 mL of the same minimal medium described previously. In addition, 1 g vanillic acid was added to the aqueous phase. The contents of the extraction vessel were mixed thoroughly and the aqueous phase continuously pumped back through the column. Incubation of the column contents at approximately 30° C. was achieved by jacketing the column with silicon tubing and pumping water through at a temperature of 34° C. The concentration of vanillin in both the oil and aqueous phase inside the extraction vessel was assayed (hplc, as described above) at intervals over an eight day period. Results, expressed as total vanillin yield from the system, were as follows: 24 hours, 113 mg; 48 hours, 140 mg; 72 hours, 269 mg; 96 hours, 385 mg; 168 hours, 597 mg; 192 hours, 566 mg.

The suitability of the system of example 8 for long-term continuous use is demonstrated by Example 9.

EXAMPLE 9

Continuous Production of Vanillin Using ISPR

A spore suspension of *Aspergillus fumigatus* (Zyl 747) was used to inoculate 3 liters of a minimal medium (ingredients described in Example 9 except for the addition of 3.3 gL$^{-1}$ vanillic acid rather than 1.5 g) in a fermenter (5 L working volume). The fermenter contents were stirred without pH control at 30° C. with the dissolved oxygen concentration being maintained at 60% of saturation throughout the process. Assay was by hplc as described above. After 24 hours incubation, 0.15 gL$^{-1}$ vanillin was detected in solution. At this time 2 liters of sunflower oil containing 0.5 gL$^{-1}$ vanillic acid was added to the fermenter and incubation was continued as described previously. Over a period of 28 days, the oil phase in the fermenter was removed at frequent intervals and replaced with fresh oil containing 0.5 gL.$^{-1}$ vanillic acid Vanillin production expressed as the total vanillin yield from the system was as follows:

| Time (hours) | Vanillin yield (g) |
| --- | --- |
| 48 | 0.64 |
| 72 | 1.43 |
| 96 | 2.71 |
| 168 | 4.60 |
| 192 | 5.12 |
| 216 | 5.58 |
| 240 | 6.20 |
| 264 | 6.87 |
| 336 | 9.16 |
| 360 | 10.32 |
| 384 | 11.50 |
| 408 | 12.25 |
| 432 | 12.80 |
| 504 | 13.80 |
| 575 | 14.50 |
| 665 | 16.26 |

After 665 hours the experiment was terminated; however, the fungus was still actively producing vanillin.

G) Use of *Pseudomonas putida* for Vanillic Acid Production

EXAMPLE 10

Conversion of Ferulic Acid to Vanillic Acid

A nutrient agar plate culture of *Pseudomonas putida* (zyl 503) was used a source of inoculum for 50 ml of growth medium (5 g ferulic acid; 20 g glucose; 2 g KH$_2$PO$_4$; 5 g (NH$_4$)$_2$SO$_4$; 0.2 g NaCl; 0.22 g MgSO$_4$; 0.015 g CaCl$_2$; 1 ml trace elements solution; 10 ml vitamins solution, made up to 1 liter with 0.2 M, pH 7.0 phosphate buffer) in a 250 ml conical shake flask. The culture was incubated at 30° C. shaking at 250 rpm and assayed by hplc as described above. As the reaction proceeded, additional amounts of ferulic acid were added as follows: 24.5 hours 0.25 g; 48 hours 0.125 g; 72 hours 0.05 g; 90 hours 0.25 g; 96 hours 0.5 g. Substrate and product concentrations were measured as being the following: 20.5 hours, ferulic acid 2.71 gl$^{-1}$, vanillic acid 2.08 gl$^{-1}$; 24.5 hours, ferulic acid 1.51 gl$^{-1}$, vanillic acid 3.01 gl$^{-1}$; 48 hours, ferulic acid 2.4 gl$^{-1}$, vanillic acid 7.0 gL$^{-1}$; 72 hours, ferulic acid 2.08 gl$^{-1}$, vanillic acid 9.5 gL$^{-1}$; 96 hours ferulic acid 4.47 gL$^{-1}$, vanillic acid 12.11 gL$^{-1}$; 160 hours, ferulic acid 4.45 gL$^{-1}$, vanillic acid 19.05 gL$^{-1}$.

EXAMPLE 11

Production of Vanillic Acid From Maize Fibre

To 30 g maize fibre in a 250 ml conical flask was added 100 ml of 8% w/v citric acid solution. The flask contents were heated at 85° C. with efficient mixing for 16 hours. After this time, the stirred maize fibre suspension was neutralised by the dropwise addition of sodium hydroxide solution (10M). A hydrolytic enzyme preparation (500 μl, Biofeed Plus, Novo Nordisk) was added to the suspension and the whole incubated at 45° C. with continued mixing for 24 hours. Analysis was by hplc as described above. After 24 hours 3.3 gl$^{-1}$ ferulic acid was detected in solution.

A culture of *Pseudomonas putida* (zyl 503) grown on nutrient agar was used to inoculate a 250 ml shake flask containing 50 ml of minimal salts medium (4 g ferulic acid; 20 g glucose; 5 g (NH$_4$)$_2$SO$_4$; 0.2 g NaCl; 2 g K$_2$HPO$_4$; 0.22 g MgSO$_4$; 0.015 g CaCl$_2$; 1 ml trace elements solution; 10 ml vitamins solution made up to 1 liter with pH 7.0 phosphate buffer 0.2 M. The flask contents were incubated at 30° C. shaking at 250 rpm for 24 hours. After this time the culture was harvested by centrifugation (4000×g, 20 minutes), washed once with 0.2 M pH 7.0 phosphate buffer to remove residual non maize derived ferulic or vanillic acid and finally resuspended in 2 ml of the same buffer (×25 concentration). This concentrated cell suspension was added to a 20 ml aliquot of the hydrolysed maize suspension described above contained in a 100 ml conical flask. The concentration of ferulic acid in solution was measured as 2.8 gl$^{-1}$ prior to incubation at 30° C. with shaking at 250 rpm. The concentration of vanillic acid present throughout the incubation period was measured as being the following: 4 hours, 0.11 gl$^{-1}$; 24.5 hours, 1.44 gL$^{-1}$; 29.5 hours, 1.98 gL$^{-1}$; 31 hours, 2.0 gL$^{-1}$.

H) Transformations of Other Substrates

The conversion of ferulic acid into vanillic acid as in example 1 is the conversion of a cinnamic acid (AR—CH=CH—CO$_2$H) to a benzoic acid (AR—CO$_2$H). This can be applied to other cinnamic acids, e.g. coumaric acid (4-hydroxycinnamic acid) and caffeic acid (3,4-dihydroxycinnamic acid).

EXAMPLE 12

4-Hydroxybenzoic Acid From Coumaric Acid

A seed stage culture of *Rhodotorula glutinis* (Zyl 702) was grown for 24 hours at 30° C. with shaking at 200 rpm in a 250 mL shake flask containing 50 mL of a minimal medium (as defined in Example 1). This culture was used to inoculate (2%) a 250 mL shake flask containing 50 mL of the same minimal medium with the addition of 200 mg coumaric acid to give a final concentration of 4 gL$^{-1}$. Incubation conditions were as described previously and assay was by hplc as described above. Substrate and product concentrations were measured as the following: 18 hours, coumaric acid 1.75 gL.$^{-1}$, 4-hydroxybenzoic acid 1.28 gL$^{-1}$, 3,4 dihydroxybenzoic acid 0.27 gL.$^{-1}$; 22 hours, coumaric acid 0.36 gL$^{-1}$, 4-hydroxybenzoic acid 1.92 gL.$^{-1}$, 3,4-dihydroxybenzoic acid 0.44 gL.$^{-1}$; 23 hours, coumaric acid 0.12 gL.$^{-1}$, 4-hydroxybenzoic acid 2.10 gL.$^{-1}$, 3,4-dihydroxybenzoic acid 0.47 gL.$^{-1}$.

The conversion of vanillic acid to vanillin as in example 4 is the conversion of a hydroxybenzoic acid to a hydroxybenzaldehyde. This can be applied to other benzoic acids, particularly hydroxybenzoic acids, e.g. 4-hydroxybenzoic acid (as produced in Example 12) or 3,4-dihydroxybenzoic acid (protocatechuic acid).

EXAMPLE 13

Conversion of 4-Hydroxybenzoic Acid to 4-Hydroxybenzaldehyde and 4-Hydroxybenzyl Alcohol A culture of *Zygorhynchus moelleri* (Zyl 851), grown on yeast malt agar, was used to inoculate a 250 mL conical flask containing 42 mL of culture medium containing 100 mg 4-hydroxybenzoic acid. The culture broth was incubated at 30° C. with shaking at 200 rpm. The progress of the reaction was assayed by hplc as described above. Substrate and product concentrations were measured as being the following: 24 hours, 4-hydroxybenzoic acid 2.26 gL, 4-hydroxybenzaldehyde trace amount, 4-hydroxybenzyl alcohol trace amount; 42 hours, 4-hydroxybenzoic acid 1.06 gL$^{-1}$, 4-hydroxybenzaldehyde 0.53 g L$^{-1}$, 4-hydroxybenzyl alcohol 0.55 gL$^{-1}$; 66 hours, 4-hydroxybenzoic acid 0.1 gL$^{-1}$, 4-hydroxybenzaldehyde trace amount, 4-hydroxybenzyl alcohol 2.6 gL$^{-1}$.

EXAMPLE 14

Conversion of 4-Hydroxybenzoic Acid to 4-Hydroxybenzaldehyde

A culture of *Trichoderma koningii* (Zyl 751) grown on yeast malt agar, was used to inoculate 50 mL of a minimal medium (as defined in Example 4a) in a 250 mL conical flask. Prior to inoculation, 150 mg (3 gL$^{-1}$) 4-hydroxybenzoic acid was added to the medium followed by incubation of the whole at 30° C. with shaking at 200 rpm. Assay was by hplc and tlc as described above. After approximately 30 hours incubation, hplc analysis detected 0.3 gL$^{-1}$ 4-hydroxybenzaldehyde in solution. This observation was further supported by tlc analysis which revealed the presence of material at R$_f$ 0.59 consistent with a reference sample of 4-hydroxybenzaldehyde. The observed product also gave a positive colour reaction with dinitrophenylhydrazine solution.

EXAMPLE 15

Conversion of 3,4-Dihydroxybenzoic Acid to 3,4-Dihydroxybenzaldehyde

A culture of *Zygorhynchus moelleri* (Zyl 851), grown on yeast malt agar, was used in inoculate a 250 mL conical flask containing 50 mL of culture medium containing 100 mg vanillic acid. The culture broth was incubated at 30° C. with shaking at 200 rpm. The progress of the reaction was assayed by hplc as described above. After 42 hours incubation, approximately 500 of the vanillic acid had been converted to vanillyl alcohol. At this time, 100 mg of 3,4-dihydroxybenzoic acid (e.g. from Example 12, or extracted from onion skins) was added to the culture and incubation continued. After a further 6 hours incubation a new product corresponding to 3,4-dihydroxybenzaldehyde was detected at a concentration of approximately 0.20 gL$^{-1}$. After 24 hours this product concentration had increased slightly to approximately 0.025 g L$^{-1}$. After 48 hours the 3,4-dihydroxybenzaldehyde had been lost from the solution.

EXAMPLE 16

Conversion of Benzoic Acid to Benzaldehyde

In a 1 liter flask, 200 mL of medium, (50 g glucose; 5 g $(NH_4)_2SO_4)_4$; 2 g $K_2HPO_4$; 0.2 g NaCl; 0.22 g $MgSO_4$; 0.015 g $CaCl_2$ 1 ml trace element solution, 1 mL; 10 ml vitamins solution; made up to 1 liter with deionised water), was inoculated with a 10 µL loopful of spores of *Trichoderma koningii* (Zyl 751) after the addition of 50 mg of benzoic acid. This was incubated at 30° C. with shaking at 200 rpm. By hplc analysis, benzaldehyde was first detected in the culture broth at 25 hours incubation. Over the next 5 hours benzaldehyde concentration rose to 0.165 g/L; at this time a concentration of 0.1 g benzyl alcohol was also present in the solution.

The conversion of vanillyl alcohol into the aldehyde in example 3 can also be applied to other benzyl alcohols, e.g. 4-hydroxybenzyl alcohol as produced in example 14.

EXAMPLE 17

Conversion of 4-Hydroxybenzyl Alcohol to 4-Hydroxybenzaldehyde

The methodology described in Example 17 was followed but at the 24 hour stage of growth of the organism 4-hydroxybenzyl alcohol was added to the flask to give a final concentration of 1 mg/mL. Monitoring the progress of the reaction by hplc showed that the amount of substrate dropped to 10% of the original after a further 28 hours at which stage 4-hydroxybenzaldehyde had reached a concentration of 0.37 mg/mL.

NB the yields of the aldehydes in examples 14–17 could doubtless be improved by the use of ISPR.

I) Selective Screening for Organisms Producing Aldehydes From Carboxylic Acids
i) Preparation of Agar Plates Minimal salts agar: 20 g glucose; 5 g $(NH_4)_2SO_4$; 2 g $K_2HPO_4$; 0.2 g NaCl; 0.22 g $MgSO_4$; 0.015 g $CaCl_2$; 10 ml trace element solution; 1 ml vitamins solution; 20 g agar and 2 g vanillic or ferulic acid made up to 1 liter with either deionised water (fungal isolation) or with 0.2M, pH 7.0, sodium phosphate buffer (bacterial isolation).

Filter paper (Whatman No.1) was cut into discs with a diameter of 90 mm and sterilised by autoclaving. Single discs were placed into 90 mm sterile petri dishes prior to the pouring of a minimal salts agar described above.
ii) Preparation of Soil Samples To 2 ml deionised water was added approximately 100 mg soil. The resulting suspension was mixed thoroughly (vortex mixer) allowed to stand at room temperature (22° C.) for 1 hour followed by further mixing to distribute suspended material. The macroscopic solids were allowed to settle for approximately 10 minutes and the supernatant (100 µl) applied to the prepared minimal salts agar plates using a spread plate technique. Plates were incubated at 28° C. until colony development was observed (approx. 5 days)
iii) Selective Visualisation of Aldehyde Producing Strains In order to visualise vanillic acid or ferulic acid biotransformation products the following procedure was followed:

Agar was lifted from the base of each petri dish by inserting a spatula beneath the filter paper disc, followed by the injection of 1 ml of dinitrophenyl hydrazine (DNP) solution (0.4% DNP in 2M HCl). The agar was replaced in the dish and the DNP solution allowed to permeate through the agar. Colonies producing aldehyde products were visualised by the presence of an orange/red zone surrounding the colony against a pale yellow background. Colonies producing alcohol products were visualised by the presence of a dark yellow zone surrounding the colony, against the pale yellow background.

What is claimed is:

1. A method of converting a first composition comprising ferulic acid into a second composition comprising vanillin, said method comprising treating said first composition with *Pseudomonas putida* IMI 382568 under conditions such that ferulic acid is converted into vanillin, and the vanillin accumulates in the culture medium.

2. A method according to claim 1 wherein said strain is capable of producing both vanillic acid and vanillin of from ferulic acid, the ratio thereof being pH-dependent; and wherein a pH is selected and maintained which relatively favors accumulation of vanillic.

3. A method according to claim 1 including a preliminary step of obtaining said first composition comprising ferulic acid from a plant material by a process comprising:
   (a) treating the plant material to produce a solution containing a ferulic acid ester; and
   (b) treating said solution with an enzyme composition having ferulic acid esterase activity under conditions such that ferulic acid esters are converted into ferulic acid.

4. A method according to claim 3 wherein said enzyme composition having ferulic acid esterase activity is one derived from species of Aspergillus or from *Humicola insolens*.

5. A method according to claim 4 wherein the enzyme is derived from *Humicola insolens* and treatment is effected in the pH range 6–7.

6. A method according to claim 1 wherein said conversion into vanillin is effected in an aqueous phase which is contacted with an organic phase which extracts said vanillin.

7. A method of converting a first composition comprising ferulic acid into a second composition comprising vanillin, said method comprising treating said first composition with a strain of *Pseudomonas putida* under conditions such that ferulic acid is converted into vanillin, and the vanillin accumulates in the culture medium wherein said strain is capable of producing both vanillic acid and vanillin from ferulic acid, the ratio thereof being pH-dependent; and wherein a pH is selected and maintained which relatively favours accumulation of vanillin.

8. A method according to claim 7 wherein said selected pH is greater than 8.0.

9. A method according to claim 8 wherein said selected pH is about pH 8.5.

10. A method according to claim 7 wherein said conversion into vanillin is effected in an aqueous phase which is contacted with an organic phase which extracts said vanillin.

11. A method according to claim 7 wherein said strain is *Pseudomonas putida* IMI 382568.

12. A method according to claim 8 wherein said plant material is selected from the group consisting of maize, wheat, sugar beet and rice materials.

13. A method according to claim 12 wherein said plant material comprises fibre, bran or straw.

14. A method according to claim 8 wherein in step (a) the plant material is treated with a solution containing citric acid.

15. A method according to claim 14 wherein said plant material is treated in the temperature range 50–250° C.

16. A method according to claim 8 wherein the plant material comprises sugar beet fibre and step (a) comprises heating in water.

17. A method of producing a composition containing vanillin from a plant material, said process comprising a preliminary step of obtaining a first composition comprising ferulic acid from a plant material by a process comprising:
   a. treating the plant material to produce a solution containing a ferulic acid ester; and
   b. treating said solution with an enzyme composition having ferulic acid esterase activity under conditions such that ferulic acid esters are converted into ferulic acid; and a subsequent step of converting said first composition comprising ferulic acid into a second composition comprising vanillin, said subsequent step comprising treating said first composition with *Pseudomonas putida* under conditions such that ferulic acid is converted into vanillin, and the vanillin accumulates in the culture medium.

18. A method according to claim 17 wherein said strain is *Pseudomonas putida* IMI382568.

19. A method according to claim 17 wherein said strain is capable of producing both vanillic acid and vanillin from ferulic acid, the ratio thereof being pH-dependent; and wherein a pH is selected and maintained which relatively favours accumulation of vanillin.

20. A method according to claim 17 wherein said conversion into vanillin is effected in an aqueous phase which is contacted with an organic phase which extracts said vanillin.

21. *Pseudomonas putida* IMI382568 or a mutant thereof capable of converting ferulic acid into vanillin.

* * * * *